(12) United States Patent
Pobortchi et al.

(10) Patent No.: US 7,408,635 B2
(45) Date of Patent: Aug. 5, 2008

(54) OPTICAL MEASUREMENT METHOD AND DEVICE

(75) Inventors: Vladimir Pobortchi, Tsukuba (JP); Toshihiko Kanayama, Tsukuba (JP); Tetsuya Tada, Tsukuba (JP)

(73) Assignee: National Institute of Advanced Industrial Science and Technology (JP)

( * ) Notice: Subject to any disclaimer, the term of this patent is extended or adjusted under 35 U.S.C. 154(b) by 219 days.

(21) Appl. No.: 10/570,367

(22) PCT Filed: Sep. 3, 2004

(86) PCT No.: PCT/JP2004/012840

§ 371 (c)(1),
(2), (4) Date: Mar. 2, 2006

(87) PCT Pub. No.: WO2005/024391

PCT Pub. Date: Mar. 17, 2005

(65) Prior Publication Data

US 2007/0013907 A1     Jan. 18, 2007

(30) Foreign Application Priority Data

Sep. 5, 2003   (JP) .............................. 2003-313901

(51) Int. Cl.
   *G01J 3/44*      (2006.01)
   *G01N 21/65*     (2006.01)
(52) U.S. Cl. ...................................... 356/301
(58) Field of Classification Search .................. 356/301; 348/79, 29; 359/368; 250/306
   See application file for complete search history.

(56) References Cited

U.S. PATENT DOCUMENTS

| 6,144,028 | A  | 11/2000 | Kley |
| 6,339,217 | B1 | 1/2002  | Kley |
| 6,545,276 | B1 | 4/2003  | Sasaki |
| 2002/0154301 | A1 | 10/2002 | Shen et al. |

FOREIGN PATENT DOCUMENTS

JP    58-210546 A    12/1983

(Continued)

*Primary Examiner*—F. L. Evans
*Assistant Examiner*—Abdullahi Nur
(74) *Attorney, Agent, or Firm*—Patterson & Sheridan, LLP

(57) ABSTRACT

An optical measurement of a crystalline sample to be measured. The sample is irradiated with an exciting light from the polarization direction in which the Raman scattering is prohibited by the selection rule. When a metal probe is brought to proximity to the sample to be measured, the selection rule is eased locally only in the proximity portion near the probe end in order that Raman scattering becomes active. Thus, a Raman signal only from the proximity portion near the probe end is detected. An optical measurement apparatus having an optical arrangement for measuring a signal light re-emitted from a sample to be measured when the sample is irradiated with an exciting light is provided. The optical measurement apparatus comprises a means for limiting the polarization state of the exciting light or signal light and a means for bringing a metal probe near the sample to be measured. The optical measurement apparatus is used to measure the signal light obtained by locally easing the limitation on the polarization state by bringing the metal probe near the sample. Therefore, Raman scattering light from silicon or the like can be measured with high space-resolution exceeding the light diffraction limit.

41 Claims, 13 Drawing Sheets

FOREIGN PATENT DOCUMENTS

| | | |
|---|---|---|
| JP | 1-16378 B2 | 3/1989 |
| JP | 10-506457 | 6/1998 |
| JP | 2000-298132 A | 10/2000 |
| JP | 2001-194286 A | 7/2001 |
| JP | 2004-177133 A | 6/2004 |
| WO | WO 96/03641 | 2/1996 |
| WO | WO 02/68919 A | 9/2002 |

(a)

(b)

(a)

(b)

A-A (a)

(b)

OPTICAL MEASUREMENT METHOD AND DEVICE

TECHNICAL FIELD

This invention relates to a method of measuring optical characteristics and, particularly, Raman spectra of a sample with a spatial resolution higher than the resolution of ordinary optical microscopes and to a device for implementing the method.

BACKGROUND ART

In recent years, study has been vigorously forwarded in the fields of nano-structures and nano-devices, and a spectrophotometric technology featuring a high resolution has been desired for evaluating properties of a variety of samples in these fields. In the silicon devices, for example, strain in Si seriously affects the device characteristics such as mobility and the like. Therefore, it is very important to know spatial distribution of the strain in Si device with a high resolution. One of the strain measurement methods is based on the Raman measurement. The Raman measurement is based on a principle that a peak position of a Raman signal shifts depending upon the strain. Upon mapping peak positions of Raman signals, therefore, it is allowed to know the distribution of strain.

The optical measurement with a high spatial resolution has heretofore been conducted by using a microscope. However, the above microscopic optical measurement encounters a barrier of diffraction limit which makes it difficult to accomplish the space resolution of finer than one micron. In modern silicon devices, the structural sizes are reaching the orders of submicrons and nanometers, and a measuring method of a higher resolution is desired. In recent years, therefore, various attempts have been made for improving the spatial resolution relying upon the near-field spectrophotometry by using a probe such as an optical fiber.

This method uses a near-field light leaking from a very small aperture at the end of the probe. Therefore, when it is attempted to observe maintaining a resolution of finer than 100 nm, the aperture size, too, must be decreased to be smaller than 100 nm, resulting in a very great loss of light quantity and arousing such a serious difficulty in the measurement that the method can be applied to only those samples that produce large signals. In the case of the Raman measurement of silicon, in particular, the optical fiber itself contains silicon which is a cause of disturbing the emission of Raman signals making it further difficult to take a measurement.

To solve this difficulty, one of the technologies proposed in the field of Raman spectroscopy uses a metallic AFM (atomic force microscope) probe. According to this method, Raman signals are enhanced only near the end of the probe due to a local electric field at an end of the metal probe, enhancing the space resolution. In this method, a large enhancing effect is obtained when two metals are brought close to each other maintaining a very small gap and when a sample to be measured is placed in the gap. Therefore, though the result can be obtained to some extent in the measurement of molecules and ultra-fine particles, the method cannot still be applied to the measurement of solid materials. This is because the sample to be measured which is a solid material cannot be placed between the two metals described above. Besides, strong signals in the far visual field are excited at positions away from the metal probe and conceal the signals in the near field.

The following patent document 1 discloses technology which uses a transmission type electron microscope to detect fine crystalline distortion in semiconductors. The image obtained by the transmission type electron microscope can be converted into a digital image, and the pattern can be calculated by two-dimensional Fourier transform.

[Patent document 1] JP-A-2000-65762

DISCLOSURE OF THE INVENTION

It is an object of this invention to solve the problem that in the near-field optical measurement, it is very difficult to detect very weak light such as of the Raman measurement.

According to the present invention, a method for solving the above problem is found by a technique that will be described below. That is, an exiting light is caused to fall on a single crystalline substrate sample such that a polarization direction thereof is prohibited by the selection rule. In the Raman scattering, for example, if the exiting light is caused to fall on the (001) plane of single crystalline silicon such that the polarization direction thereof is in the [100] direction so as to detect the scattered light that is polarized in the [100] direction only, the first-order Raman scattered light appearing near a wave number 520 cm$^{-1}$ is prohibited by the selection rule. This method uses strict selection rules for the first-order Raman scattering of crystalline Si.

In the Raman scattering, similarly, if the exciting light is incident on the (001) plane of single crystalline silicon and polarized in the [100] direction so as to detect the scattered light that is polarized in the [100] direction only, the first-order Raman band of Si at 520 cm$^{-1}$ is forbidden by the selection rule. Further, if the exciting light is incident on the (001) plane of single crystalline silicon from the direction perpendicular to the plane and polarized in the [110] direction so as to detect the scattered light that is polarized in a direction at right angles therewith only, the first-order Raman band of Si at 520 cm$^{-1}$ is forbidden by the selection rule. For the (110) plane, further, for both the incident and scattered lights polarized parallel to the [001] direction the Raman band at 520 cm$^{-1}$ is forbidden.

Here, if a metallic probe is brought close to the irradiated portion, the polarization of the local electric field near the tip will differ from the polarization of the incident light whereby the Raman scattering becomes active and its intensity is enhanced by an electric field of a surface plasmon induced at the end of the probe. Signals from portions away from the probe are forbidden and are very weak. However, the Raman scattering is permitted on a portion close to the probe. Therefore, the signals near the end of the probe can be separated and taken out. That is, the Raman signals from only the portion near the end of the probe can be detected to realize a high resolution. The resolving power depends on the diameter of the probe tip. The resolving power of the order of nanometers can be obtained if the diameter of the tip of the probe is sufficiently decreased.

Further, if just the end of a probe is made of a material having high scattering efficiency for the exciting light but the other portions of the probe being made of a material having low scattering efficiency, the incident light is scattered mainly by the end of the probe. For the scattered light, the polarization direction rotates from the basic exciting light and, besides, the traveling direction of light changes, whereby the selection rule is relaxed, the Raman scattering is activated and the intensity is enhanced by an electric field of surface plasmon induced at the end of the probe. Signals from portions away from the probe are forbidden and are very weak. However, if the probe is brought sufficiently close to the sample, the range where the scattered light reaches from the end of the probe is limited to the vicinity of the probe, and the Raman scattering is permitted at that portion. Therefore, the signals near the end of the probe can be separated and taken out. It is effective to use short wavelength light, i.e., an ultraviolet ray as the exciting light to increase the absorption coefficient of the sample and to decrease the penetration depth of the scattered light into the sample. Employment of this configuration makes it possible to detect Raman signals from only a portion near the end of the probe to realize a high spatial resolution. The resolution depends on the diameter of fine particles carried at the end of the probe. The resolution of the order of nanometers can be obtained if the diameter of the fine particles is sufficiently small.

A manner in which the selection rule is relaxed by the probe can be proved by the theoretic calculation. FIG. 1 shows the calculated results for the cases where light of a wavelength of 400 nm falls onto the end of a silver probe of a spheroid shape and where the polarization directions and intensities of near-field are calculated for different polarization directions of incident light (arrow at an upper part of the ellipse in each drawing): (a) polarization of the incident light is parallel to, (b) perpendicular to, and (c) tilted by 45 degrees with respect to the rotary axis (long axis) of the probe. The polarization direction and intensity of the near-field light are expressed by the direction and length of the arrow on the line at the top of the ellipse in the drawings. It is shown that when the polarization of incident light is parallel to the long axis, a strong near-field light parallel with the direction of incident polarization is induced. When the polarization of incident light is perpendicular to the long axis, a weak near-field light with the polarization parallel to that of the incident light is induced. When the polarization of incident light is tilted by 45 degrees, a strong near-field light is induced in the direction that is not parallel to the direction of the incident polarization.

Therefore, even when the incident light has a polarization direction in which the Raman scattering is prohibited, the induced near-field light possesses the Raman-active polarization direction if the angle between the polarization direction and the axis of the probe is set to be, for example, 45 degrees as described above, and there can be observed Raman scattered signals induced by the near-field light only. In a practical device, the end of the probe is not a perfect spheroid but has some fine ruggedness. Therefore, even without correct control of the polarization direction of incident light in respect to the probe axis, a near field is induced in a polarization direction different from the incident polarization direction. Namely, the Raman selection rule can be relaxed even by simply bringing the probe close to the sample.

This invention solves the above problems in a manner as described above. More concretely, the invention solves the problems by a method and a device as described below. Namely, an optical measurement method of the invention includes an optical arrangement for measuring a signal light from a sample to be measured by irradiating the sample with exciting light, wherein the optical arrangement is the one that prohibits the signal light by a selection rule, and a probe is brought close to the sample to be measured to locally relax the selection rule in only a portion near the end of the probe thereby to obtain the signal light.

Another optical measurement method of the invention includes an optical arrangement for measuring a signal light from a sample to be measured by irradiating the sample with exciting light, wherein the optical arrangement is the one that prohibits the signal light by a selection rule, and a probe having an end portion and other portions made of different materials at least on the surfaces thereof is brought close to the sample to be measured to measure the signal light.

A further optical measurement method of the invention is concerned with the above optical measurement method, wherein the end portion has a material in the surface thereof different from the other portions due to the surface treatment.

A further optical measurement method of the invention is concerned with the above optical measurement method, wherein the end portion is made of a material different from that of the other portions.

A further optical measurement method of the invention is concerned with the above optical measurement method, wherein the probe uses, in the end portion thereof, a material having a large efficiency for scattering the exciting light and uses, in other portions thereof, a material having a small efficiency for scattering the exciting light.

A further optical measurement method of the invention is concerned with the above optical measurement method, wherein the probe carries, on the end portion thereof, fine particles of a material different from that of the other portions.

A further optical measurement method of the invention is concerned with the above optical measurement method, wherein the other portions are made of a material transparent for the excitation light.

A further optical measurement method of the invention is concerned with the above optical measurement method, wherein the other portions are made of a glass or a plastic material.

A further optical measurement method of the invention is concerned with the above optical measurement method, wherein the fine particles are fine metal particles.

A further optical measurement method of the invention is concerned with the above optical measurement method, wherein the metal is any one of silver, gold, platinum or copper.

A further optical measurement method of the invention is concerned with the above optical measurement method, wherein the end portion and the vicinity thereof are immersed in a solution having a refractive index close to a refractive index of a material of the other portions, and a measurement is taken by decreasing the scattering of the exciting light in the portions other than the end portion of the probe.

A further optical measurement method of the invention is concerned with the above optical measurement method, wherein the exciting light is ultraviolet light.

A still further optical measurement method of the invention causes exciting light to fall on a crystalline sample to be measured from a polarization direction in which the Raman scattering is prohibited by the selection rule, and brings a probe close to the sample to be measured to locally relax the selection rule in only a portion near the end of the probe thereby to activate the Raman scattering and to obtain Raman signals from only the portion near the end of the probe.

A further optical measurement method of the invention is concerned with the above optical measurement method, wherein the sample to be measured is a flat plate of a (001) orientation having a crystal structure which is a diamond structure or a zinc-blende structure, and scattered light of [100] polarization is detected with the exciting light being polarized in the [100] direction.

A further optical measurement method of the invention is concerned with the above optical measurement method, wherein the sample to be measured is a flat plate of a (001) orientation having a crystal structure which is a diamond structure or a zinc-blende structure, the exciting light is incident on the sample in a direction [00-1] and is polarized in a direction [100] or [010], and signal light scattered in a direction [001] which is the same polarization direction as the exciting light is detected.

A further optical measurement method of the invention is concerned with the above optical measurement method, wherein the sample to be measured is a flat plate of a (001) orientation having a crystal structure which is a diamond structure or a zinc-blende structure, the exciting light is incident on the sample in a direction [00-1] and is polarized in a direction [110] or [1-10], and signal light scattered in a direction [001] which is a polarization direction at right angles with the exciting light is detected.

An yet further optical measurement method of the invention is concerned with the above optical measurement method, wherein exciting light is caused to fall on a (001) plane of single crystalline silicon from a direction perpendicular to the plane such that the exciting light is polarized in the [110] direction and scattered light polarized in a direction at right angles therewith only is detected, or exciting light polarized in parallel with the [001] direction is caused to fall on the (110) plane to prohibit the Raman scattering polarized in parallel with the [001] direction.

A further optical measurement method of the invention is concerned with the above optical measurement method, wherein the probe is scanned to measure a spatial distribution of Raman signals.

A further optical measurement method of the invention is concerned with the above optical measurement method, wherein the probe is the one coated with silver or gold.

A further optical measurement method of the invention is concerned with the above optical measurement method, wherein the sample to be measured is any one of silicon, diamond, germanium, Si—Ge mixed crystal, ZnS, ZnO, BN, BP, AlP, GaN, GaP, GaAs, InP, InAs, MSe (M=Be, Cd, Hg, Zn, Mn) or a mixed crystal thereof.

Further, an optical measurement device equipment of the invention includes an optical arrangement for measuring a signal light from a sample to be measured by irradiating the sample to be measured with exciting light, comprising means for limiting the polarized state of the exciting light or the signal light, and means for bringing a probe close to the sample to be measured, wherein the probe is brought close to the sample to be measured to measure the signal light.

Another optical measurement device of the invention is concerned with the above optical measurement device, wherein the probe has an end portion and other portions made of different materials at least on the surfaces thereof.

A further optical measurement device of the invention is concerned with the above optical measurement device, wherein the end portion has a material in the surface thereof different from the other portions due to the surface treatment.

A further optical measurement device of the invention is concerned with the above optical measurement device, wherein the end portion is made of a material different from that of the other portions.

A further optical measurement device of the invention is concerned with the above optical measurement device, wherein the probe uses, in the end portion thereof, a material having a large efficiency for scattering the exciting light and uses, in other portions thereof, a material having a small efficiency for scattering the exciting light.

A further optical measurement device of the invention is concerned with the above optical measurement device, wherein the probe carries, on the end portion thereof, fine particles of a material different from that of the other portions.

A further optical measurement device of the invention is concerned with the above optical measurement device, wherein the other portions are made of a material transparent for the exciting light that is irradiated.

A further optical measurement device of the invention is concerned with the above optical measurement device, wherein the other portions are made of a glass or a plastic material.

A further optical measurement device of the invention is concerned with the above optical measurement device, wherein the fine particles are fine metal particles.

A further optical measurement device of the invention is concerned with the above optical measurement device, wherein the metal is any one of silver, gold, platinum or copper.

A further optical measurement device of the invention is concerned with the above optical measurement device, wherein the end portion and the vicinity thereof are immersed in a solution having a refractive index close to a refractive index of a material of the other portions, and a measurement is taken by decreasing the scattering of the exciting light in the portions other than the end portion of the probe.

A further optical measurement device of the invention is concerned with the above optical measurement device, wherein the exciting light is ultraviolet light.

A further optical measurement device of the invention is concerned with the above optical measurement device, wherein the sample to be measured is a flat plate of a (001) orientation having a crystal structure which is a diamond structure or a zinc blende structure, and scattered light of [100] polarization is detected with the exciting light being polarized in the [100] direction.

A further optical measurement device of the invention is concerned with the above optical measurement device, wherein the sample to be measured is a flat plate of a (001) orientation having a crystal structure which is a diamond structure or a zinc blende structure, the exciting light is incident on the sample in a direction [00-1] and is polarized in a direction [100] or [010], and signal light scattered in a direction [001] which is the same polarization direction as the exciting light is detected.

A further optical measurement device of the invention is concerned with the above optical measurement device, wherein the sample to be measured is a flat plate of a (001) orientation having a crystal structure which is a diamond structure or a zinc blende structure, the exciting light is incident on the sample in a direction [00-1] and is polarized in a direction [110] or [1-10], and signal light scattered in a direction [001] which is a polarization direction at right angles with the exciting light is detected.

A further optical measurement device of the invention is concerned with the above optical measurement device, wherein the probe is scanned to measure a spatial distribution of Raman signals.

A further optical measurement device of the invention is concerned with the above optical measurement device, wherein the probe is the one coated with silver or gold.

A further optical measurement device of the invention is concerned with the above optical measurement device, wherein the sample to be measured is any one of silicon, diamond, germanium, Si—Ge mixed crystal, ZnS, ZnO, BN, BP, AlP, GaN, GaP, GaAs, InP, InAs, MSe (M=Be, Cd, Hg, Zn, Mn) or a mixed crystal thereof.

A further optical measurement device of the invention is concerned with the above optical measurement device, wherein provision is made of means for varying a distance between the probe and the surface of the sample to be measured, and means for taking a difference between the intensity of signal light of when the probe is brought close to the surface of the sample to be measured and the intensity of signal light when the probe is separated away therefrom.

A further optical measurement device of the invention is concerned with the above optical measurement device, wherein provision is made of means for causing the exciting light to fall on the surface of the sample to be measured nearly perpendicularly thereto and for detecting the signal light from the surface of the sample nearly perpendicularly thereto.

A further optical measurement device of the invention is concerned with the above optical measurement device, wherein provision is made of means for bringing the probe close to the surface of the sample to be measured from a tilted direction.

Being constituted as described above, this invention solves the problem that in the near-field optical measurement, it is very difficult to detect very weak light such as Raman measurement and, particularly, solves the problem that in the near-field optical measurement by using a metal probe, the far field signals conceal signals in the near field to deteriorate the spatial resolution of measurement, and makes it possible to measure the Raman scattered light from silicon which could not be accomplished so far maintaining spatial resolution higher than the diffraction limit of light.

BEST MODE FOR CARRYING OUT THE INVENTION

According to this invention, Raman signal from silicon can be measured with a spatial resolution better than the light diffraction limit by an optical measurement method which includes an optical arrangement for measuring a signal light from a sample to be measured by irradiating the sample with exciting light, wherein the optical configurations are the ones that prohibit the signal light by the selection rule, and a probe having an end portion and other portions made of different materials is brought close to the sample to be measured to measure the signal light, by using an optical measurement device which includes an optical configuration for measuring a signal light from a sample to be measured by irradiating the sample with exciting light, comprising means for limiting the polarization of the exciting light or the signal light, and means for bringing a probe close to the sample to be measured, the probe having an end portion and other portions made of different materials and being brought close to the sample to be measured to measure the signal light.

EXAMPLE 1

Figure 1:
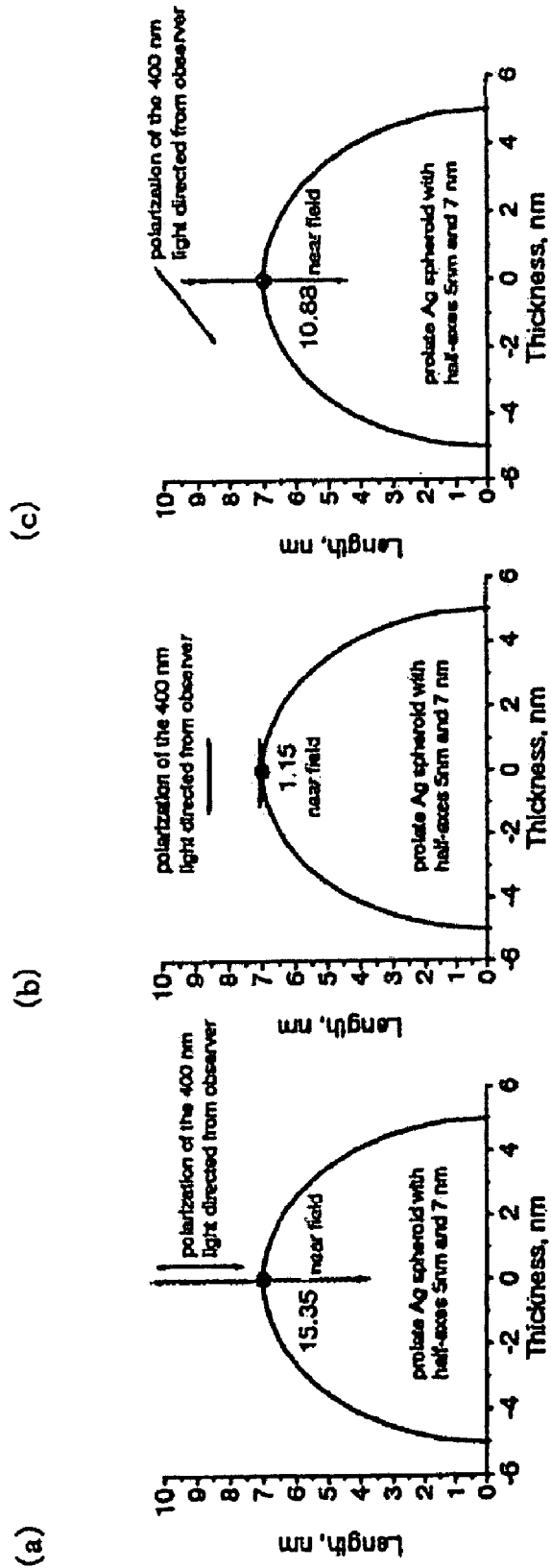
FIG. 1 is a diagram showing the calculated results for the cases where light of a wavelength of 400 nm is caused to fall on the end of a silver probe of a spheroid shape and where the polarization directions and intensities of near-field light induced by the interaction of light and probe are calculated when the polarization direction of incident light is (a) in parallel with, (b) perpendicular to, and (c) tilted by 45 degrees with respect to, the direction of the rotation axis (long axis) of the probe.
Figure 2:
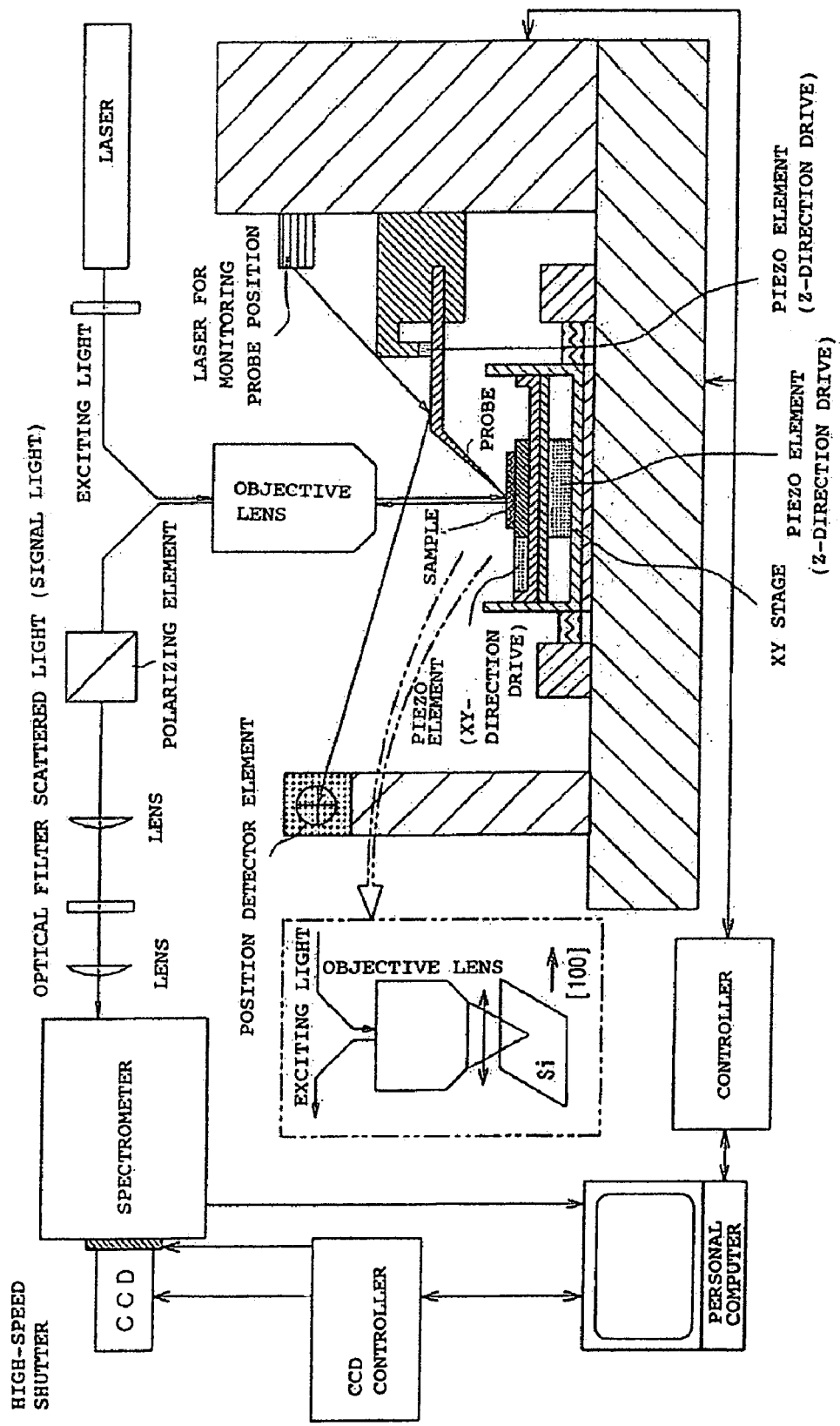
FIG. 2 is a diagram schematically illustrating the arrangement for optical measurement according to the invention.

FIG. 2 is a diagram schematically illustrating the arrangement for measurement. The AFM probe coated with silver is mounted on a piezo element and can be vibrated up and down by signals from a controller. Further, a piezo element is mounted on a stage on which a sample holder is mounted, and can be driven up and down and right and left by signals from the controller. The exciting laser beam is focused on the surface of a sample by an objective lens, and the AFM probe coated with silver is brought close to the focusing portion. The operation of the AFM probe is controlled by the light from a laser diode and by a detector. As shown, the laser beam for excitation is caused to so fall as to be polarized in [100]. Of the scattered light collected by the objective lens, the scattered light polarized in [100] only is guided to a spectrometer and is separated.

More concretely, the laser beam of 514.5 nm or 632.8 nm is caused to fall on a (001) substrate of Si perpendicularly thereto in a manner that the polarization direction is the [100] direction, is focused by the objective lens into 1 to 2 μm on the surface of the sample, and the AFM probe coated with silver and having an end of a diameter of 100 nm is placed thereon. The arrangement of measurement is such that the scattered light is focused by the objective lens and is guided to the spectrometer.

Figure 3:
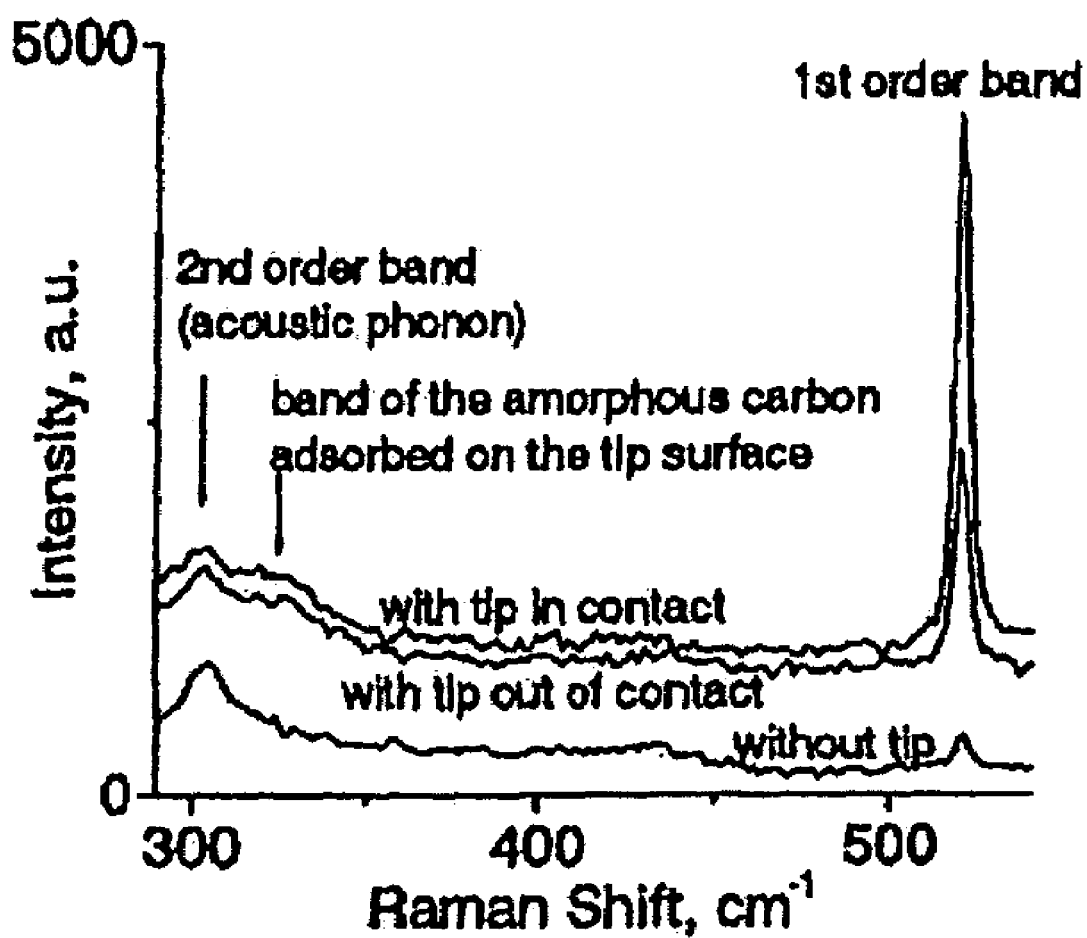
FIG. 3 is a graph illustrating Raman spectra measured without a probe (lower graph); with a probe retracted away from the surface of the sample (middle graph), and with the probe is in contact with the surface of the sample (upper graph) in the forbidden polarization configuration (Si (001) surface; polarizations of the incident and scattered lights are parallel to the [100] axis).

FIG. 3 illustrates Raman spectra in comparison when the metal probe in this arrangement is separated away from the surface of the sample by about 500 nm and when the metal probe is brought close to the surface of the sample. That is, there are shown a Raman spectrum (lower graph) measured without an AFM probe, a spectrum (intermediate graph) of when the silver probe is separated away from the surface of the sample by about 500 nm and a spectrum (upper graph) of when the silver probe is in contact in the forbidden arrangement on the Si (001) surface. Without the metal probe, the peak is almost suppressed at the wavenumber of 520 $cm^{-1}$. When the metal probe is brought into contact, however, the peak is observed at 520 $cm^{-1}$. The peak appears because the selection rule is locally broken at the end of the probe and, hence, the signal is from the sample near the end of the probe. When the probe is separated away by 500 nm, too, there appears a peak though it is considerably weaker than that of when the probe is brought in contact. This is due to the fact that when the exciting light hits the metal probe, the polarization direction is affected not only by the near-field light but also slightly by the light of far field. To obtain the effect of the near-field light only, therefore, a difference should be detected between the intensity of signal light of when the metal probe is brought close to the surface of the sample and the intensity of signal of when it is separated away thereby to take out only those signals due to the near field and, accordingly, to improve the spatial resolution and the S/N ratio. The S/N ratio of differential signal can be improved by using, for example, a piezo element, the sample being vibrated up and down at 10 Hz maintaining an amplitude of 500 nm. Synchronized with the probe movement, the CCD sends data to a computer, and the differential signal is accumulated 100 times to improve the S/N ratio by 10 folds.

EXAMPLE 2

Figure 4:
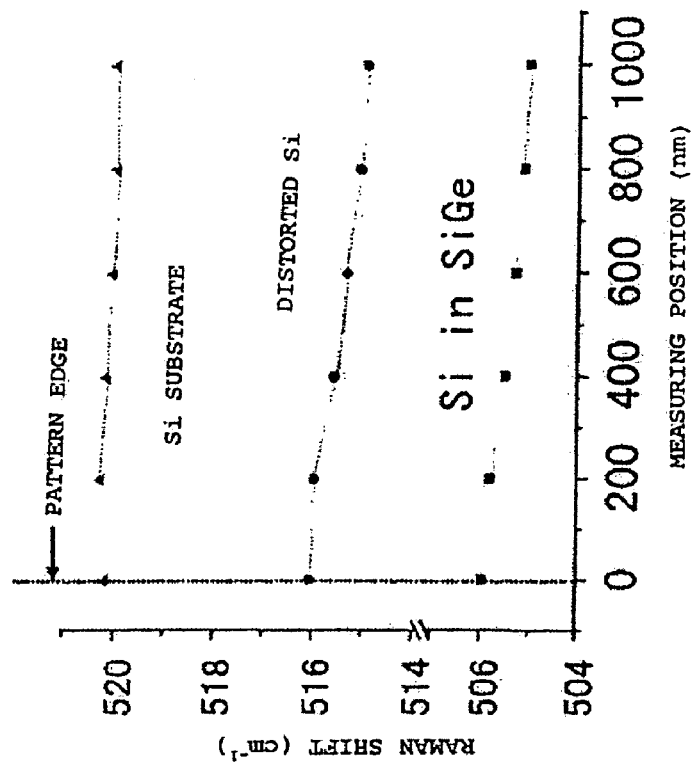
FIG. 4(a) is a graph illustrating the structure of the SOI island with the strained Si film on the top and a change in the Raman spectra near the edge of the island (a), and (b) is a graph illustrating dependence of the Raman shift of Si substrate, $Si_{1-x}Ge_x$ and strained Si vs. the distance from the edge of the island.
Figure 4:
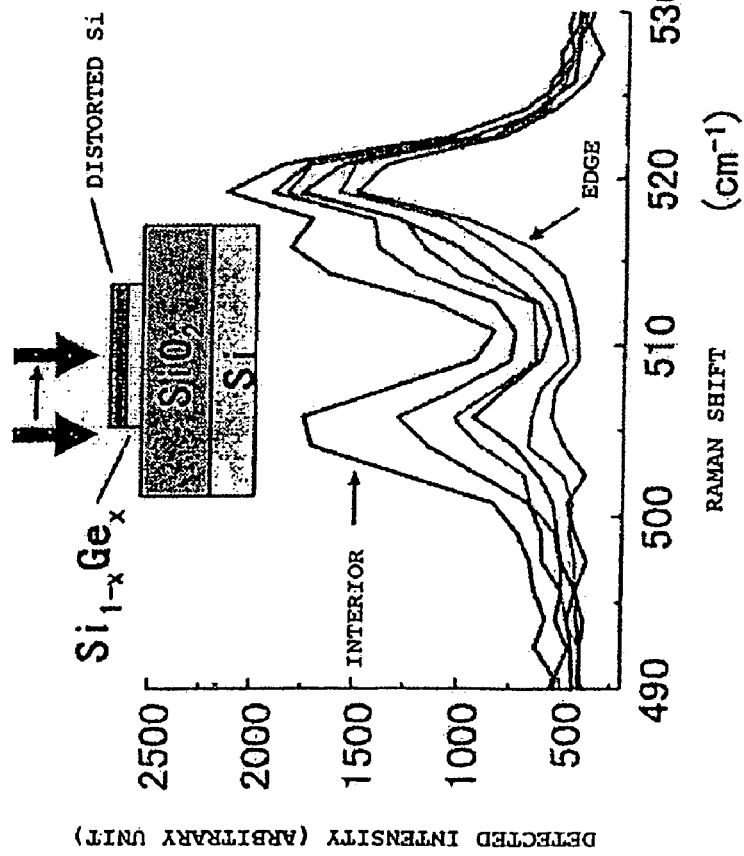

The following measurement is conducted to prove a high spatial resolution of the measurement method of this Example. Referring to FIG. 4(a), the sample is a 5 μm wide island of a strained SOI (silicon-on-insulator) thin film formed by epitaxially growing Si in a thickness of 14 nm on the (001) surface of SiGe (Ge composition of 28%) of a thickness of 40 nm. Here, a laser beam of 514.5 nm is caused to fall in a manner that the polarization direction thereof is in parallel with [100]. The scattered light of which the polarization direction is in parallel with [100] only is detected by using a polarizer. FIG. 4(a) illustrates changes in the Raman spectra near the edge of the SOI island, and (b) illustrates changes in the Raman shift.

Strained Si and Si have different lattice constants, therefore the peak position of the Raman spectra shifts from ordinary 520 $cm^{-1}$ to ~515 $cm^{-1}$. The probe is scanning from the edge of the island to its interior region while monitoring the peak of 515 $cm^{-1}$. At the edge of the pattern, the Raman peak is centered at ~516 $cm^{-1}$, which, however, becomes ~515 $cm^{-1}$ toward the interior region. The spatial resolution is about 100 nm.

EXAMPLE 3

The measurement is taken in the same manner as in Example 2 but using a tip having diameter of 50 nm. The spatial resolution is about 50 nm.

EXAMPLE 4

Figure 5:
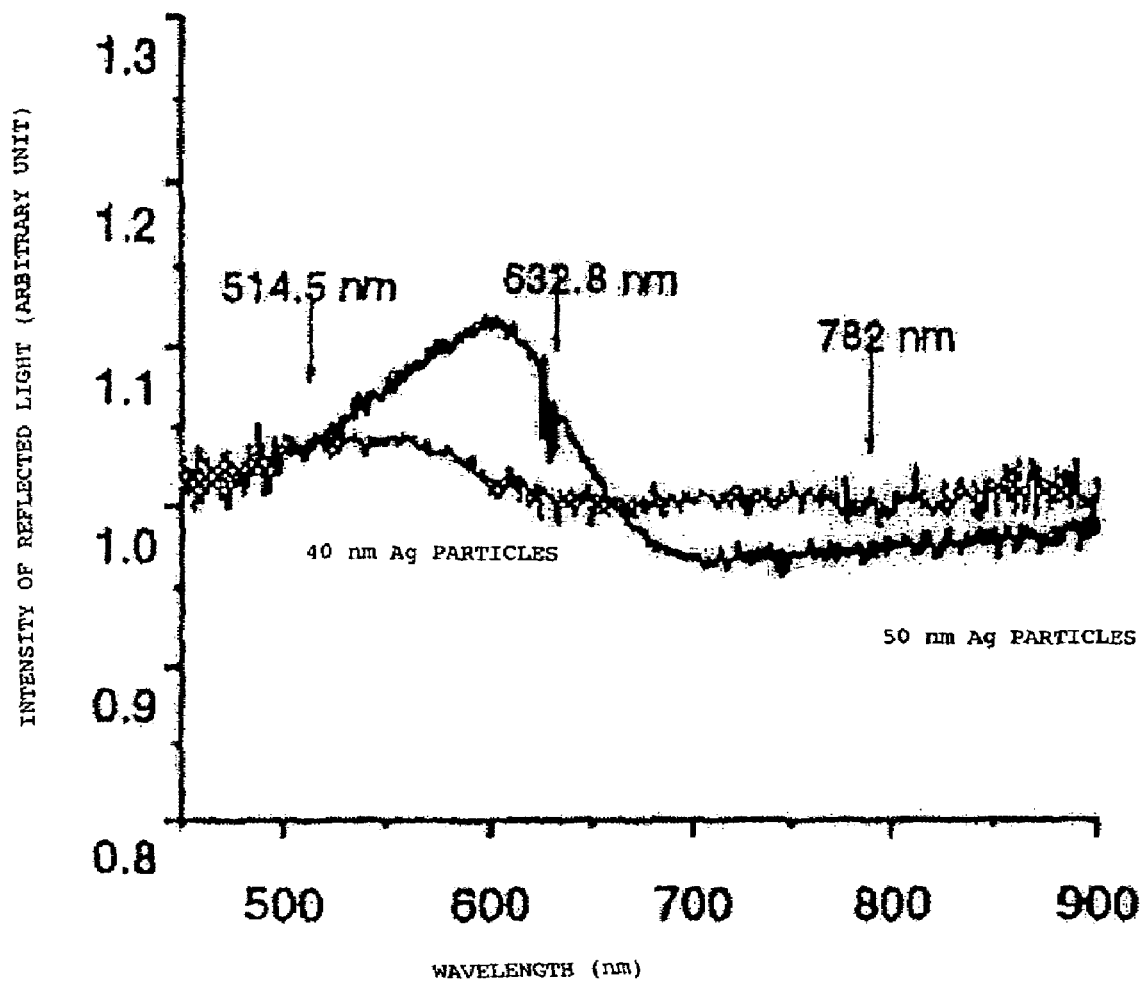
FIG. 5 is a graph illustrating the results of measuring the reflection spectra by arranging silver particles of a diameter of 50 nm and a diameter of 40 nm on an Si substrate.

Silver particles of a diameter of 50 nm and of a diameter of 40 nm are arranged on an Si substrate, and reflection spectra are measured to obtain results as shown in FIG. 5. A peak near 600 nm in the reflection spectrum of silver particles of 50 nm is caused by the excitation of plasmon, and the polarization direction of scattered light changes. With silver particles of 40 nm, on the other hand, the above peak is not observed and the polarization direction is preserved.

In this arrangement, the exciting light of a wavelength of 632.8 nm is caused to fall such that the polarization direction of the exciting light is in the [100] direction, and the Raman spectrum is measured in the arrangement for detecting the scattered light polarized in the [100] direction only (forbidden configuration for the Raman peak of 520 $cm^{-1}$). The enhancement effect is obtained only for those silver particles having a diameter of 50 nm. This is due to that the polarization direction of the exciting light changes due to the silver particles of 50 nm and the selection rule is relaxed.

Figure 6:
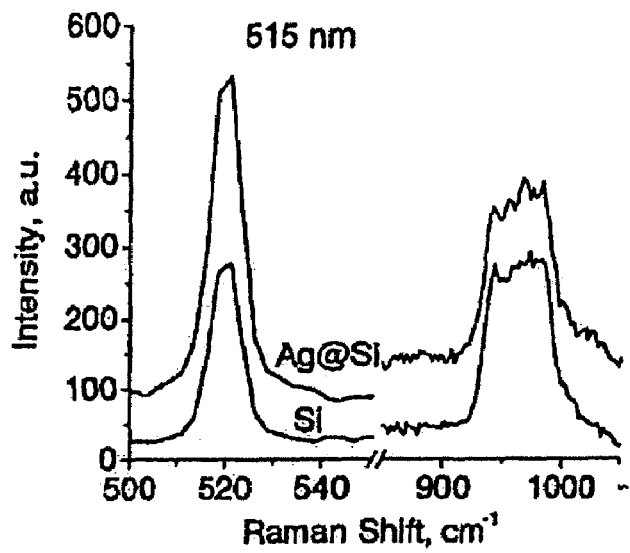
FIG. 6 is a graph illustrating Raman spectra of Si by using an Si substrate on which silver particles of a diameter of 50 nm are arranged at exciting wavelengths of 514.5 nm, 632.8 nm and 782 nm depending on a portion where the silver particles are existing and a portion where the silver particles are not existing (attention should be given to different scales of the ordinate)
Figure 6:
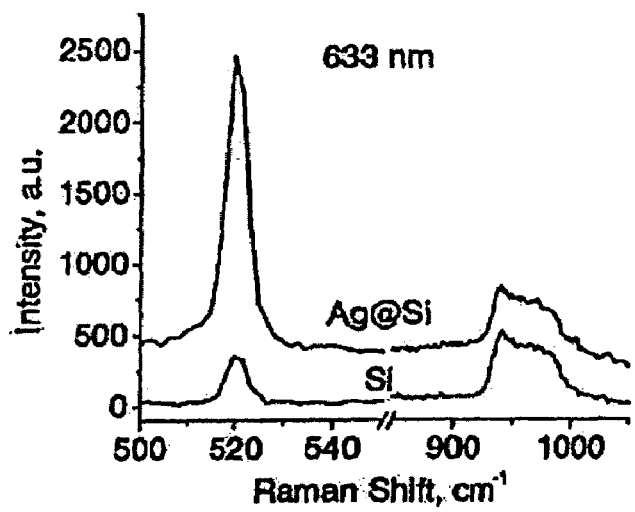
Figure 6:
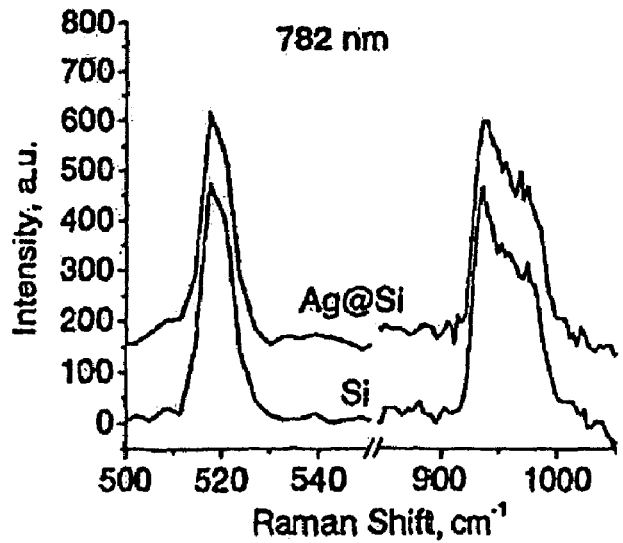

FIG. 6 shows Raman spectra of Si (forbidden polarization configuration) for Si with and without 50 nm particles for the 514.5 nm, 632.8 nm and 782 nm excitation wavelengths. In accordance with the plasmon resonance position, enhancement of the 520 $cm^{-1}$ band due to the depolarization effect is observed for the 514.5 nm and 632.8 nm excitations but is not for the 782 nm excitation. As will be understood from the reflection spectra of FIG. 5, this is due to the fact that the interaction between the exciting light and the silver particles is small at the wavelengths of 514.5 nm and 782 nm, and the polarization direction does not change. The second-order Raman band of Si centered at ~950 $cm^{-1}$ is allowed for the used polarization configuration and its intensity is not affected by the presence of the Ag particles. This band can be used as a reference for the 520 $cm^{-1}$ band intensity.

The above results are obtained for the silver particles on the Si substrate. This, however, can also be applied to a metal probe. The probe will produce better near field and better depolarization effect for the wavelengths corresponding to its surface plasmon resonance. That is, by measuring the reflectivity, the wavelength can be found at which the exciting light and the metal probe interacts each other, and a wavelength of exciting light suited for the measurement can be estimated. Further, the effect of the metal probe on the polarization of light of far field described in Example 1 can be suppressed by selecting the exciting wavelength.

Figure 7:
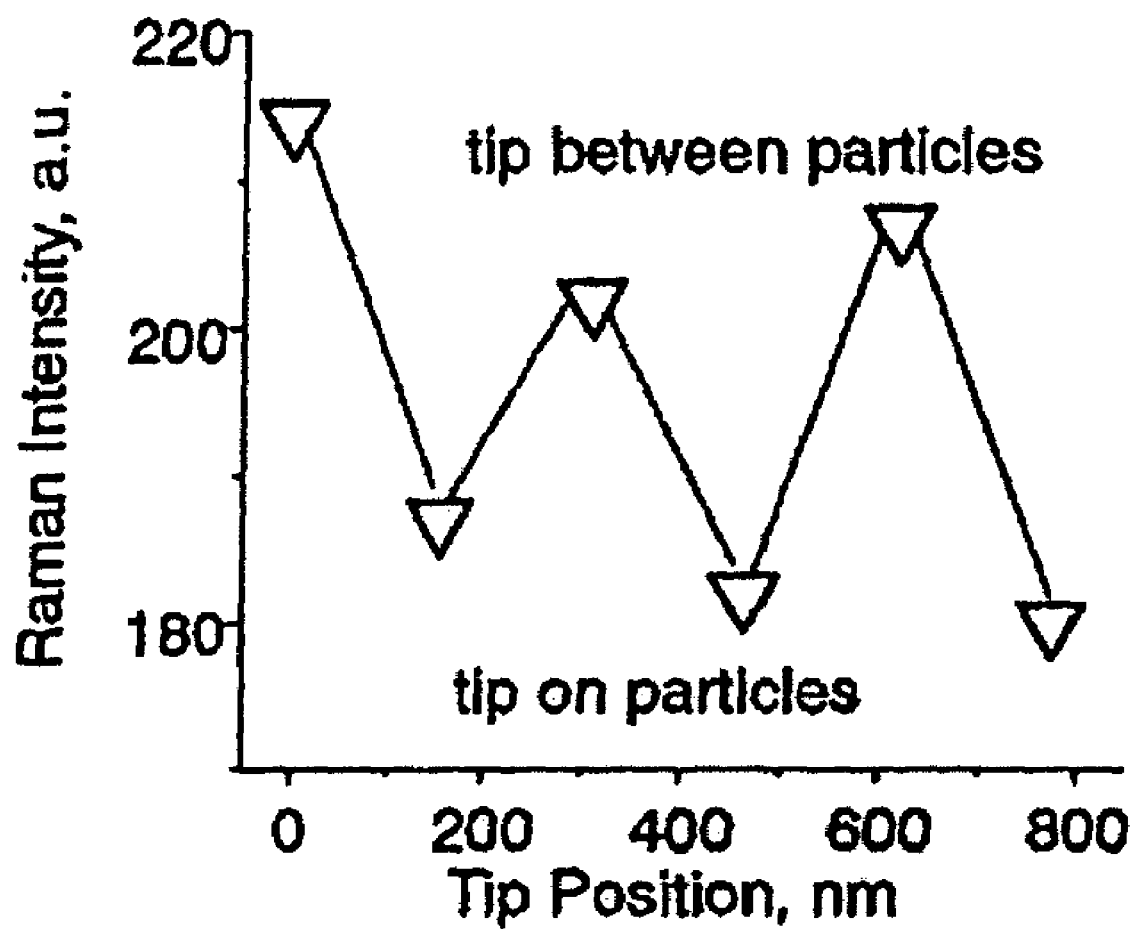
FIG. 7 is a graph drawn by plotting Raman signal intensities at 520 $cm^{-1}$ according to the method of the patent while scanning the Si substrate on which silver particles of 50 nm diameter are arranged with a spacing of 230 nm by using an AFM probe coated with silver in contact therewith.

Next, Raman intensities at 520 $cm^{-1}$ (forbidden polarization configuration) were measured while scanning the Si substrate with ~50 nm silver particles arranged in a square lattice with ~230 nm period by using an AFM probe coated with silver in the contact mode (FIG. 7). The exciting wavelength is 782 nm. This exciting wavelength is selected since the silver-coated AFM probe displays surface plasmon resonance at 782 nm due to the prolonged shape of the probe but the silver particles does not as obtained from the above experimental result (FIG. 5).

Referring to a graph of FIG. 7, when the AFM probe comes on a silver particle, the near field by the AFM probe does not reach the surface of Si and the Raman signal is not enhanced. When the AFM probe is not on the silver particle, however, the Raman signal is enhanced due to the AFM probe near field. The graph tells that the spatial resolution is 100 nm or better.

EXAMPLE 5

Figure 8:
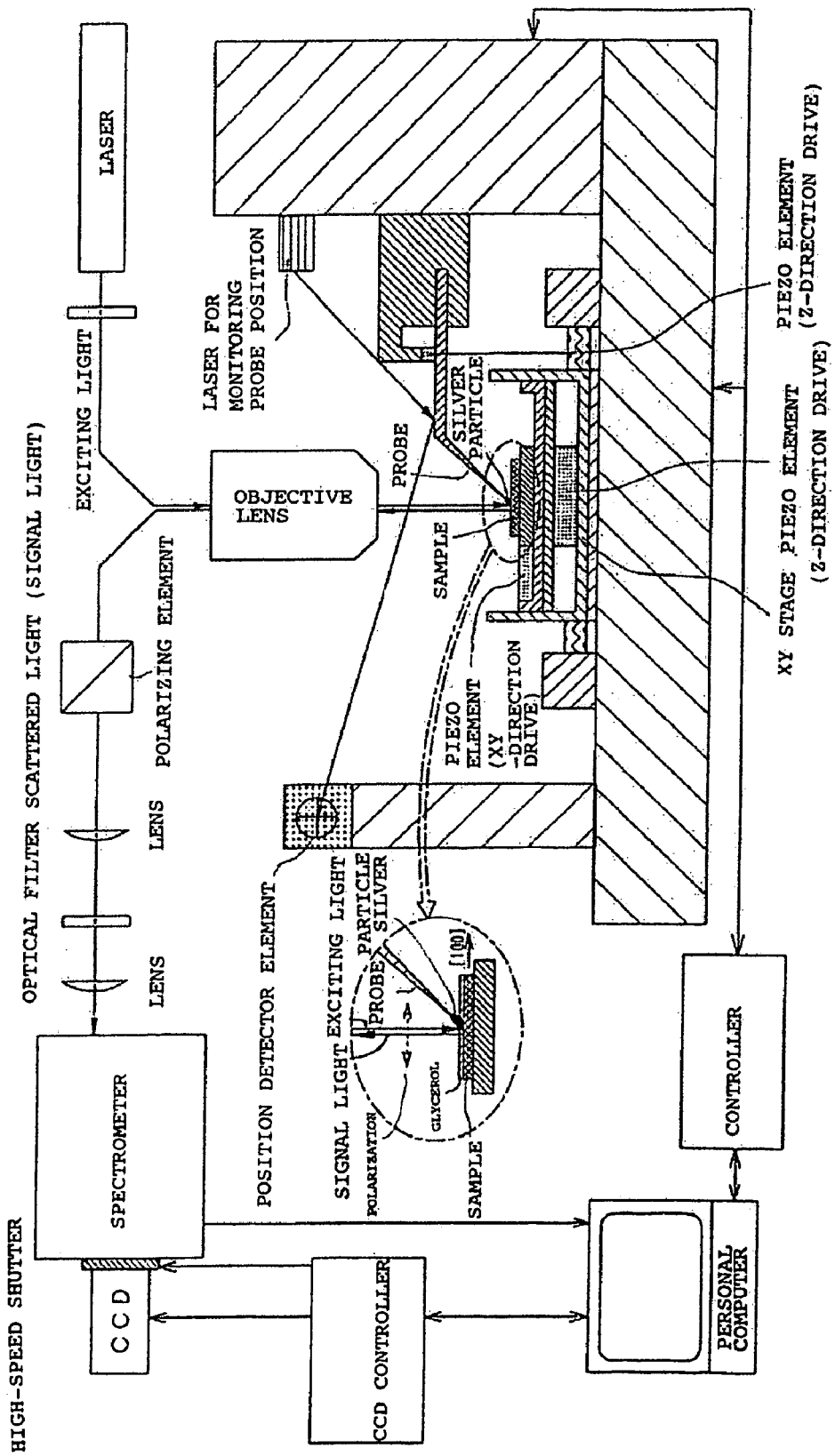
FIG. 8 is a view schematically illustrating an arrangement for optical measurement by using a probe on which silver particles are carried according to the Example of the invention mentioned below, wherein the principal configuration is the one used in the above embodiment.

FIG. 8 illustrates a further Example of the invention. The probe having a tip made of a material different from that of the other portions of the probe is brought close to the sample and locally depolarizes the incident light and relaxes the selection rules. Then, an allowed local Raman signal from the area near the end of the probe appears. In the Example of FIG. 8, the end of the probe is made of a different material on at least the surface thereof by carrying fine metal particles such as of silver, gold, platinum, copper or the like.

FIG. 8 is a diagram illustrating the arrangement for measurement. In this diagram of the arrangement for measurement, the contents of the above Examples 1 to 4 can similarly be applied except the point concerning the end of the probe and the vicinity thereof. In FIG. 8, the exciting laser beam is focused on the surface of a sample by an objective lens, and a quartz probe carrying silver particles of a diameter of about 50 nm at the end thereof, which is purchased from Nanonics Co., is brought close thereto. The operation of the probe is controlled by the light from a laser diode and by a detector. As shown in an enlarged inset in the drawing, the incident laser light is polarized in the [110] direction on the sample plane, and the scattered light is collected by the objective lens and only the component polarized perpendicular to the incident one is guided to a spectrometer. The exciting light is ultraviolet.

The laser beam of a wavelength of 364 nm polarized in the [110] direction is caused to fall normally onto a (001) substrate of Si. The laser beam is focused by the objective lens into a 1 µm spot on the surface of the sample, and the quartz probe carrying on its tip a silver particle of a diameter of about 50 nm is placed into the spot. Further, a glycerol liquid is dripped onto the surface of the sample so that the end part of the probe to be irradiated with the exciting light is immersed therein. Glycerol prevents scattering of the light by the other portions of the probe since the refractive index of the glycerol is equal to that of quartz. The light scattered by the sample is collected by the objective lens and guided to the spectrometer. Silicon exhibits a very large absorption coefficient for the light of 364 nm, and the light can penetrate into Si by only about 10 nm. Therefore, an improvement can be expected in the spatial resolution.

Figure 9:
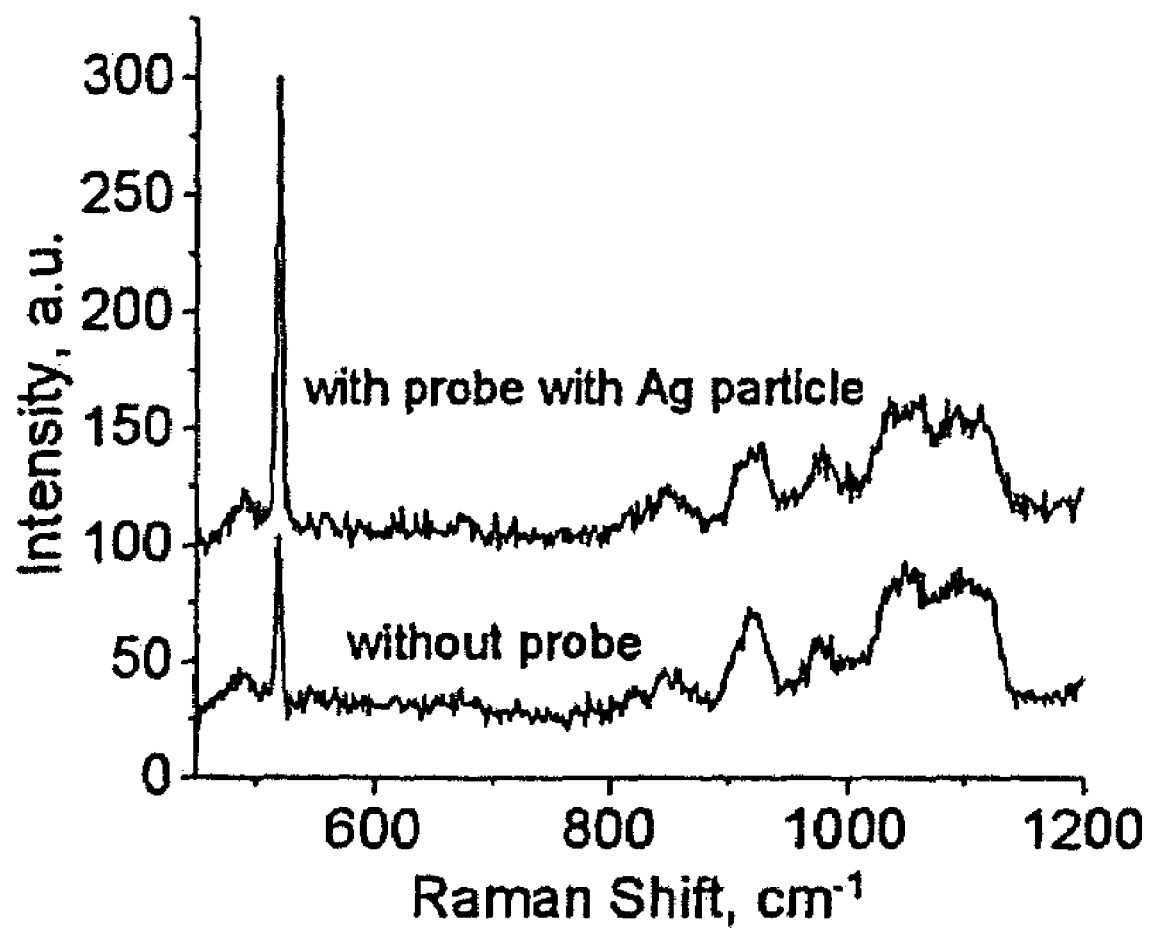
FIG. 9 is a graph illustrating the experimental results of the above Example and shows Raman spectra of Si with and without AFM probe for the 364 nm excitation and forbidden polarization configuration (incident light is polarized parallel to the [110] axis of Si but the scattered light is polarized parallel to the [1-10] axis.

FIG. 9 illustrates Raman spectra of the Si substrate with (upper graph) and without (lower graph) the described probe contacting the (001) Si surface. Without the probe, the peak at 520 cm$^{-1}$ is suppressed due to the forbidden polarization configuration. With the metal-particle-topped probe in contact, however, the peak at 520 cm$^{-1}$ is enhanced because the selection rule is broken for the exciting light that is scattered at the end of the probe. Further, peaks from 800 to 1200 cm$^{-1}$ are stemming from the glycerol.

When the sample is a flat plate parallel of the (001) orientation of a crystal with the diamond or zinc blende structure, the invention can be implemented by illuminating the sample in the [00-1] direction with the light polarized in the [100] or [010] direction, and by detecting Raman signal scattered in the [001] direction with the same polarization as the incident light. For the same sample, further, the invention can be implemented by the polarizing the incident light in the direction [110] or [1-10], and with the scattered light polarized perpendicular to the incident one, other conditions being equal. Further, the invention can be implemented when the light is incident on the (110) plane and polarized parallel to the [001] direction to prohibit the Raman scattering polarized parallel to the same [001] direction.

EXAMPLE 6

Figure 10:
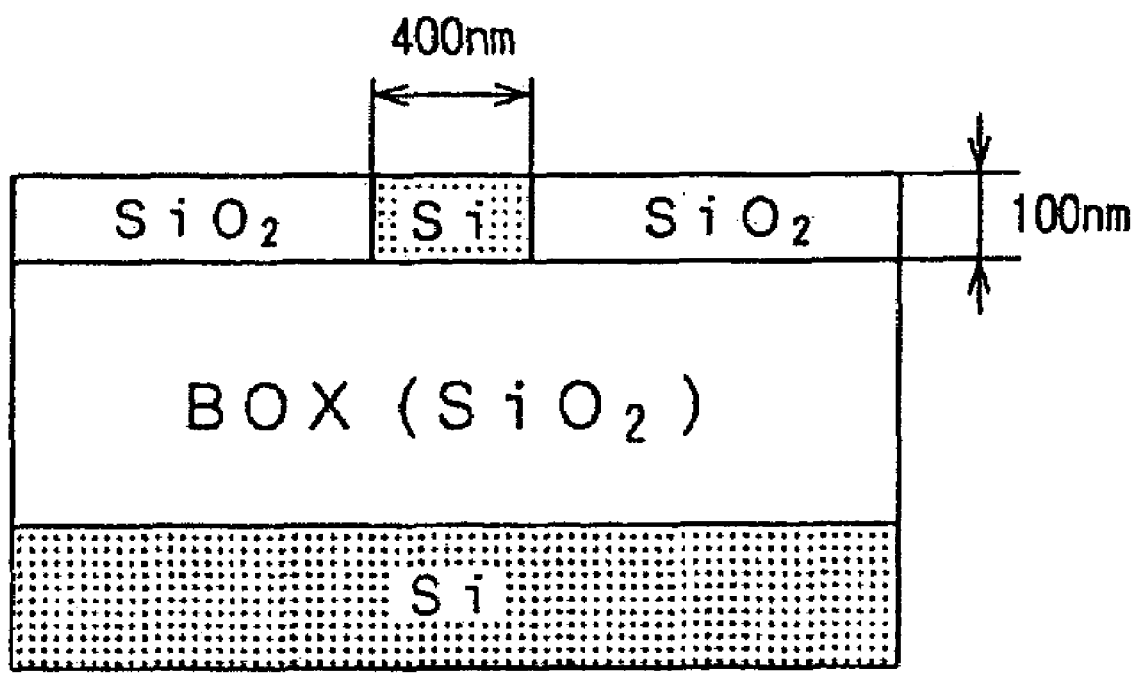
FIG. 10 is a diagram illustrating a sample structure used in a further Example of the invention.

Referring to FIG. 10, a sample forming a silicon belt of a width of 400 nm and of a thickness of 100 nm on the (110) surface of an SOI substrate is studied by the Raman microscopy using an AFM probe carrying silver particles of 50 nm diameter. The silicon belt is sandwiched by $SiO_2$ and is presumed to be distorted. It is expected that the Raman peak of silicon at 520 cm$^{-1}$ is shifted.

Figure 11:
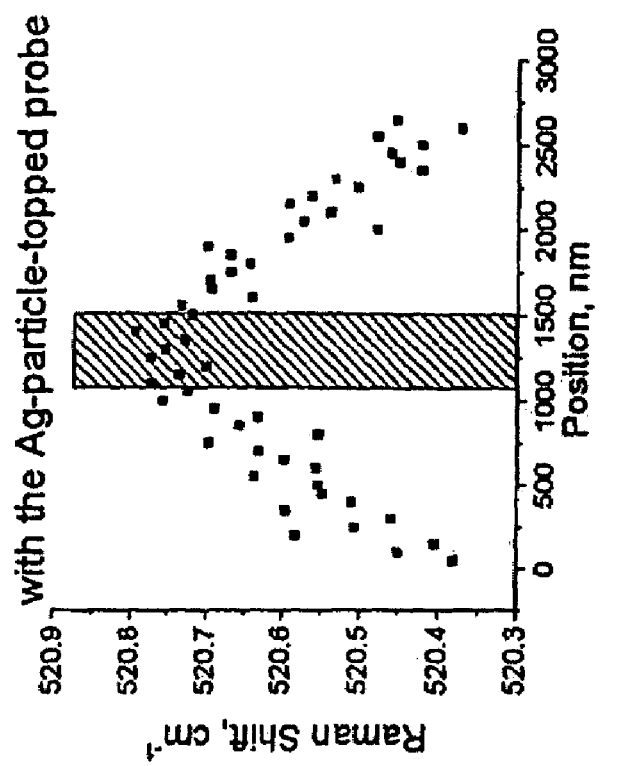
FIG. 11 is a graph illustrating the results of measurement by using the above sample, wherein (a) corresponds to the measurement without AFM probe and (b) corresponds to the measurement with the Ag-particle-topped AFM probe.
Figure 11:
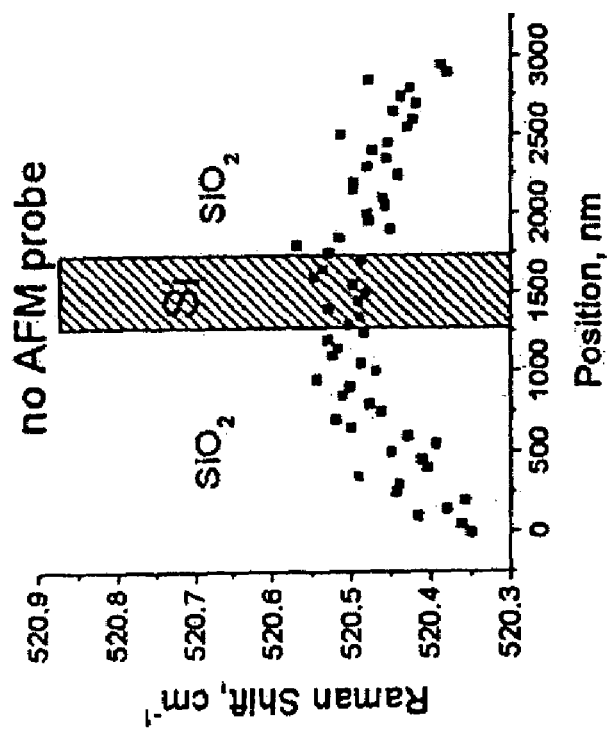

The exciting wavelength is 364 nm. The exciting light focused by the objective lens has a spot diameter of about 1 µm which is greater than the width of the belt. The arrangement for measurement is the same as that of Example 5. FIG. 11 shows, as a function of center positions of spots, the peak positions of Raman signals of when the center positions of spots are scanned at an interval of 50 nm in a direction perpendicular to the silicon belt by using the probe and without using the probe. Without the probe, changes in the Raman shift are rather weak. This is because, the beam spot diameter of the exciting light is 1 µm which is greater than the width of the belt, and the spatial resolution is not sufficient. On the other hand, On the other hand, when the silver-particle-topped AFM probe is used, the Raman shift dependence becomes more pronounced due to the improved spatial resolution.

EXAMPLE 7

Figure 12:
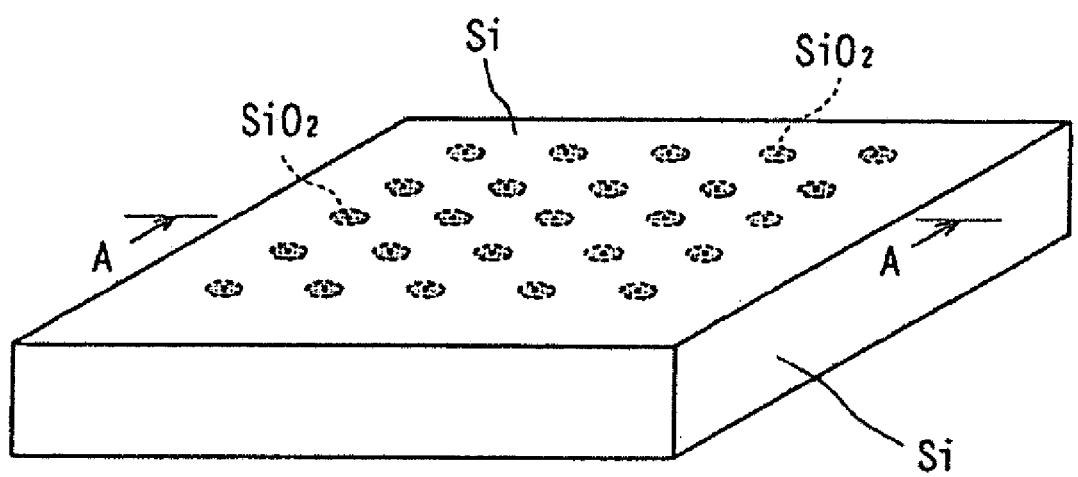
FIG. 12 is a view schematically illustrating a sample of when holes of a diameter of about 100 nm are etched in a silicon substrate and when inner walls of the holes are thermally oxidized, wherein (a) is a perspective view and (b) is a sectional view along the portion A-A in (a)
Figure 12:
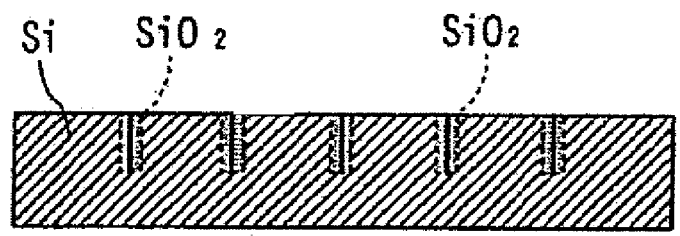
Figure 13:
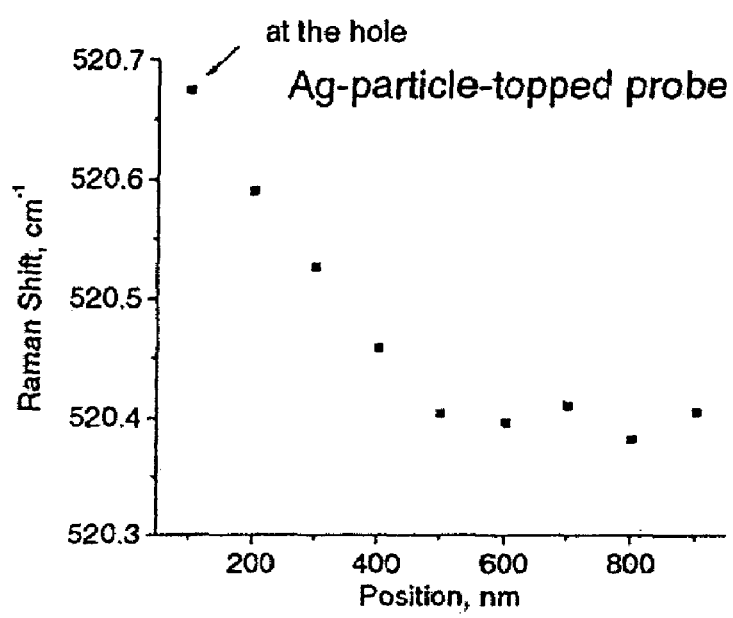
FIG. 13 is a graph illustrating dependence of the Raman shift on the probe position for (a) Ag-particle-topped AFM probe (364 nm excitation) and (b) Ag-coated AFM probe (514.5 nm excitation).
Figure 13:
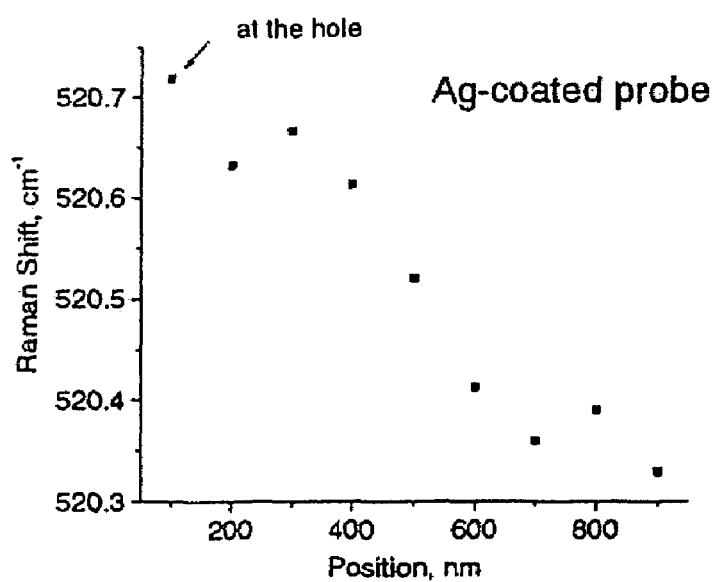

In order to confirm the improvement in the spatial resolution of Raman measurement by using a probe carrying silver particle, FIG. 12 shows a sample obtained by etching holes of diameter of 100 nm in a silicon substrate and producing stress by thermal oxidation of the inner walls of the holes. Raman measurement of the sample was taken with the silver-particle-topped AFM probe (364 nm excitation) as well as with the silver-coated probe (514.5 nm excitation). The results are as shown in the following graph. When the probe is scanned on the sample surface away from above the hole, the Raman shift changes from 520.7 cm$^{-1}$ to 520.3 cm$^{-1}$. This reflects the fact that the oxidized holes induce the stress in the surrounding silicon, stress decreasing with the distance from the hole. The exciting light has a spot size of about 1 µm from which it is concluded that the spatial resolution is improved by the use of the probe.

It will be further understood that when scanned by using the probe carrying silver particles, the peak position changes more sharply and a better spatial resolution is obtained than when scanned by using the probe coated with silver. This is due to that when the probe carrying silver particles is used, the exciting light is scattered by the end portion only.

INDUSTRIAL APPLICABILITY

This invention can be extensively utilized as an optical measurement technology featuring a high resolution for evaluating properties of a variety of samples in such fields as nano-structures and nano-devices that have been studied and developed in recent years.

The invention claimed is:

1. An optical measurement method including an optical arrangement for measuring a signal light from a sample to be measured by irradiating the sample with exciting light, wherein:

said optical arrangement is one that prohibits said signal light by a selection rule; and a probe is brought close to said sample to be measured to locally relax the selection rule in only a portion near the end of said probe thereby to obtain the signal light.

2. An optical arrangement method including an optical arrangement for measuring a signal light from a sample to be measured by irradiating the sample with exciting light, wherein:
   said optical arrangement is one that prohibits said signal light by a selection rule; and
   a probe having an end portion and other portions made of different materials at least on surfaces thereof is brought close to said sample to be measured to measure the signal light.

3. An optical measurement method according to claim 2, wherein said end portion has a material in the surface thereof different from the other portions due to the surface treatment.

4. An optical measurement method according to claim 2, wherein said end portion is made of a material different from that of the other portions.

5. An optical measurement method according to claim 2, wherein said probe uses, in the end portion thereof, a material having a large efficiency for scattering the exciting light and uses, in other portions thereof, a material having a small efficiency for scattering the exciting light.

6. An optical measurement method according to claim 4, wherein said probe carries, on the end portion thereof, fine particles of a material different from that of the other portions of the probe.

7. An optical measurement method according to claim 6, wherein the other portions are made of a material transparent for the exciting light.

8. An optical measurement method according to claim 6, wherein the other portions are made of a glass or a plastic material.

9. An optical measurement method according to claim 6, wherein said fine particles are fine metal particles.

10. An optical measurement method according to claim 9, wherein said metal is any one of silver, gold, platinum or copper.

11. An optical measurement method according to claim 5, wherein said end portion and the vicinity thereof are immersed in a solution having a refractive index close to a refractive index of a material of the other portions, and a measurement is taken by decreasing the scattering of the exciting light in the portions other than the end portion of the probe.

12. An optical measurement method according to claim 1, wherein said exciting light is ultraviolet light.

13. An optical measurement method by causing exciting light to fall on a crystalline sample to be measured from a polarization direction in which Raman scattering is prohibited by a selection rule, and bringing a probe close to said sample to be measured to locally relax the selection rule in only a portion near an end of the probe thereby to activate the Raman scattering and to detect Raman signals from only the portion near the end of the probe.

14. An optical measurement method according to claim 13, wherein said sample to be measured is a flat plate of a (001) orientation having a crystal structure which is a diamond structure or a zinc blende structure, and scattered light of [100] polarization is detected with the exciting light being polarized in the [100] direction.

15. An optical measurement method according to claim 13, wherein said sample to be measured is a flat plate of a (001) orientation having a crystal structure which is a diamond structure or a zinc blende structure, the exciting light is incident on the sample in a direction [00-1] and is polarized in a direction [100] or [010], and signal light scattered in a direction [001] which is the same polarization direction as the exciting light is detected.

16. An optical measurement method according to claim 13, wherein said sample to be measured is a flat plate of a (001) orientation having a crystal structure which is a diamond structure or a zinc blende structure, the exciting light is incident on the sample in a direction [00-1] and is polarized in a direction [110] or [1-10], and signal light scattered in a direction [001] which is a polarization direction at right angles with the exciting light is detected.

17. An optical measurement method according to claim 13, wherein exciting light is caused to fall on a (001) plane of single crystalline silicon from a direction perpendicular to the plane such that the exciting light is polarized in the [110] direction and scattered light polarized in a direction at right angles therewith only is detected, or exciting light polarized in parallel with the [001] direction is caused to fall on the (110) plane to prohibit the Raman scattering polarized in parallel with the [001] direction.

18. An optical measurement method according to claim 13, wherein said probe is scanned to measure a spatial distribution of Raman signals.

19. An optical measurement method according to claim 3, wherein said probe is coated with silver or gold.

20. An optical measurement method according to claim 1, wherein said sample to be measured is any one of silicon, diamond, germanium, Si—Ge mixed crystal, ZnS, ZnO, BN, BP, AlP, GaN, GaP, GaAs, InP, InAs, MSe (M=Be, Cd, Hg, Zn, Mn) or a mixed crystal thereof.

21. An optical measurement device comprising:
   an optical arrangement for measuring a signal light from a sample to be measured by irradiating the sample with exciting light,
   wherein the optical arrangement is one which prohibits the signal light by a selection rule; and
   means for bringing a probe close to the sample to be measured so that the selection rule is relaxed in a local region where the probe is present near the sample so as to detect the signal light.

22. An optical measurement device according to claim 21, wherein said probe has an end portion and other portions made of different materials at least on the surfaces thereof.

23. An optical measurement device according to claim 22, wherein said end portion has a material in the surface thereof different from the other portions due to the surface treatment.

24. An optical measurement device according to claim 22, wherein said end portion is made of a material different from that of the other portions.

25. An optical measurement device according to claim 24, wherein said probe uses, in said end portion thereof, a material having a large efficiency for scattering the exciting light and uses, in other portions thereof, a material having a small efficiency for scattering the exciting light.

26. An optical measurement device according to claim 24, wherein said probe carries, on said end portion thereof, fine particles of a material different from that of the other portions.

27. An optical measurement device according to claim 24, wherein the other portions are made of a material transparent for the exciting light.

28. An optical measurement device according to claim 24, wherein the other portions are made of a glass or a plastic material.

29. An optical measurement device according to claim 26, wherein said fine particles are fine metal particles.

30. An optical measurement device according to claim 29, wherein said metal is any one of silver, gold, platinum or copper.

31. An optical measurement device according to claim 22, wherein said end portion and the vicinity thereof are immersed in a solution having a refractive index close to a refractive index of a material of the other portions, and a measurement is taken by decreasing the scattering of the exciting light in the portions other than the end portion of the probe.

32. An optical measurement device according to claim 21, wherein said exciting light is ultraviolet light.

33. An optical measurement device according to claim 21, wherein said sample to be measured is a flat plate of a (001) azimuth having a crystal structure which is a diamond structure or a sphalerite structure, and scattered light of [100] polarization is detected with the exciting light being polarized in the [100] direction.

34. An optical measurement device according to claim 21, wherein said sample to be measured is a flat plate of a (001) orientation having a crystal structure which is a diamond structure or a zinc blende structure, the exciting light is incident on the sample in a direction [00-1] and is polarized in a direction [100] or [010], and signal light scattered in a direction [001] which is the same polarization direction as the exciting light is detected.

35. An optical measurement device according to claim 21, wherein said sample to be measured is a flat plate of a (001) orientation having a crystal structure which is a diamond structure or a sphalerite structure, the exciting light is incident on the sample in a direction [00-1] and is polarized in a direction [110] or [1-10], and signal light scattered in a direction [001] which is a polarization direction at right angles with the exciting light is detected.

36. An optical measurement device according to claim 21, wherein said probe is scanned to measure a spatial distribution of Raman signals.

37. An optical measurement device according to claim 23, wherein said probe is coated with silver or gold.

38. An optical measurement device according to claim 21, wherein said sample to be measured is any one of silicon, diamond, germanium, Si—Ge mixed crystal, ZnS, ZnO, BN, BP, AlP, GaN, GaP, GaAs, InP, InAs, MSe (M=Be, Cd, Hg, Zn, Mn) or a mixed crystal thereof.

39. An optical measurement device according to claim 21, wherein provision is made of:
   means for varying a distance between said probe and a surface of said sample to be measured; and
   means for taking a difference between the intensity of signal light of when said probe is brought close to the surface of said sample to be measured and the intensity of signal light of when said probe is separated away therefrom.

40. An optical measurement device according to claim 21, wherein provision is made of means for causing said exciting light to fall on a surface of said sample to be measured nearly perpendicularly thereto and for detecting the signal light from the surface of the sample nearly perpendicularly thereto.

41. An optical measurement device according to claim 21, wherein provision is made of means for bringing said probe close to a surface of said sample to be measured from a tilted direction.

* * * * *